United States Patent [19]

Scherrer et al.

[11] Patent Number: 4,526,896

[45] Date of Patent: Jul. 2, 1985

[54] TETRAZOL-5-YL 2-NITRO-3-PHENYLBENZOFURANS AND ANTIMICROBIAL USE THEREOF

[75] Inventors: Robert A. Scherrer, White Bear Lake; Richard M. Stern, Cottage Grove; Walton J. Hammar, St. Paul, all of Minn.

[73] Assignee: Riker Laboratories, Inc., St. Paul, Minn.

[21] Appl. No.: 240,871

[22] Filed: Mar. 5, 1981

Related U.S. Application Data

[63] Continuation-in-part of Ser. No. 973,150, Dec. 26, 1978, abandoned.

[51] Int. Cl.³ .................. A01N 43/64; C07D 405/04; C07D 405/06

[52] U.S. Cl. .................... 514/252; 548/250; 548/252; 548/253; 548/309; 549/467; 549/469; 546/196; 546/198; 546/315; 544/70; 544/359; 514/278; 514/255; 514/422; 514/326; 514/422; 514/326; 514/382

[58] Field of Search ........ 548/252, 253, 250; 424/269

[56] References Cited

U.S. PATENT DOCUMENTS

| | | | |
|---|---|---|---|
| 3,590,082 | 6/1971 | Sarett et al. | 548/253 |
| 3,862,134 | 1/1975 | Scherrer | 424/274 X |
| 4,067,993 | 1/1978 | Scherrer | 548/253 |
| 4,124,704 | 11/1978 | Scherrer | 424/180 |

OTHER PUBLICATIONS

Buchanan et al., J. Med. Chem., vol. 12, p. 1001, 1969.

*Primary Examiner*—Glennon H. Hollrah
*Assistant Examiner*—D. B. Springer
*Attorney, Agent, or Firm*—Donald M. Sell; James A. Smith; Robert W. Sprague

[57] ABSTRACT

Antimicrobial 2-nitro-3-phenylbenzofurans wherein the benzo or the 3-phenyl portion of the molecule is bonded to an alkylene or an oxyalkylene group which is in turn bonded to a basic nitrogen atom or to the nitrogen atom of an (N-lower alkanoyl)amino group.

15 Claims, No Drawings

TETRAZOL-5-YL 2-NITRO-3-PHENYLBENZOFURANS AND ANTIMICROBIAL USE THEREOF

REFERENCE TO RELATED APPLICATION

This is a continuation-in-part of copending application Ser. No. 973,150 filed Dec. 26, 1978, abandoned.

BACKGROUND OF THE INVENTION

This invention relates to a class of 2-nitro-3-phenylbenzofurans wherein the benzo or the 3-phenyl portion of the molecule is bonded to an alkylene or an oxyalkylene group which is in turn bonded to a basic nitrogen atom or to the nitrogen atom of an (N-lower alkanoyl)amino group (which are active as antimicrobial agents) and processes for their use. The nitrogen atoms in the described substituents may be part of unsubstituted amino groups, mono- or disubstituted amino groups or cyclic amines. The invention also relates to pharmaceutically acceptable salts (e.g. acid halide and quaternary ammonium salts) of the basic compounds of the invention, to the use of the compounds of the invention as antimicrobial agents and to intermediates useful in their synthesis.

Compounds containing the 2-nitro-3-phenylbenzofuran nucleus are known. See, for example, U.S. Pat. Nos. 4,022,908; 4,048,323; 4,066,782; 4,067,993 and 4,124,704. Compounds containing said nucleus which also contain a basic nitrogen-containing group or an (N-lower alkanoyl)amino group are not known, however. More specifically, compounds wherein the aromatic benzo or 3-phenyl portions of the 2-nitro-3-phenylbenzofuran nucleus is bonded to an alkylene or oxyalkylene group which is in turn bonded to a basic nitrogen atom or to the nitrogen atom of an (N-lower alkanoyl)amino group are not known.

DETAILED DESCRIPTION OF THE INVENTION

This invention relates to compounds of the formula

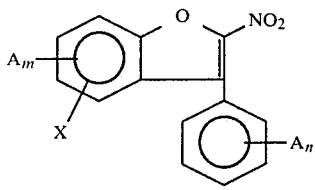

wherein
A is QR— or BD—,
R is alkylene of one or three carbon atoms or oxyalkylene of two or three carbon atoms,
Q is an unsubstituted amino group, a mono-substituted amino group, a di-substituted amino group, a cyclic amino groups or an (N-lower alkanoyl)amino group derived from a primary or secondary amine, Q containing not more than 12 carbon atoms and being bonded to R directly through a nitrogen atom therein,
B is an unsubstituted tetrazole ring,
D is a carbon-carbon bond or methylene (—CH$_2$—),
m and n are zero or one, the sum of m and n is one and
X is hydrogen, methyl or ethyl, provided that the Q—R— moiety is optionally substituted by a single carboxylic acid group,
and pharmaceutically acceptable salts of such compounds. It is the compounds in which Q is a basic nitrogen-containing group (an amine) which form the salts.

The term "lower" as used in connection with alkyl and alkylene groups herein refers to such groups containing from one to four carbon atoms. Thus, lower alkanoyl herein refers to a group containing lower alkyl (containing up to four carbon atoms) bonded to carbonyl.

The hydrogen atom in B exists in tautomeric form on either the N$^1$ or N$^2$ atom, i.e.

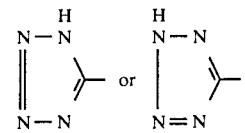

but is depicted herein, for convenience, as appearing on the N$^1$ atom.

When R is alkylene it is preferably methylene. The alkylene group may furthermore be bonded to a carboxyl group (in which case the group —R—Q is an amino acid group.

X in the compounds of the invention is preferably hydrogen or methyl.

Q preferably contains not more than 10 carbon atoms. When m is one, the group Q—R— is preferably oriented in the 5, 6 or 7 position of the benzo ring.

When n is one, the group Q—R— is preferably oriented in the 3' or 4' position of the phenyl ring. It is also preferred that when n is one, Q is amino, N-lower alkylamino or N,N-dilower alkylamino (particularly such compounds in which the lower alkyl groups are methyl.

The preferred compounds of the invention include those in which Q is selected from amino, N-lower alkylamino, N,N-dilower alkylamino, N-lower alkylamino lower alkyleneamino, N-lower alkylamino lower alkylene-N-lower alkylamino, N,N-dilower alkylamino lower alkyleneamino, pyrrolidinyl, piperidinyl, N-methylpiperazinyl, N-phenylpiperazinyl, N-hydroxyethylpiperazinyl, nipecotamido, carboxyalkylamino, prolino, lower alkyl isonipecotato, lower alkyl isonicotinato, 1-phenyl-8-N-1,3,8-triazaspiro[4,5]decan-4-onyl and pseudothiohydantoinyl.

The invention also includes the antimicrobial use of the compounds of the invention and certain compounds which are intermediates in the synthesis of the final compounds of the invention (I).

The compounds of the invention are ordinarily white or yellowish to brown or green crystalline or amorphous materials when purified. They are generally substantially insoluble in water or aliphatic hydrocarbons and are more soluble in acetone, lower alcohols, halogenated solvents, benzene, N,N-dimethylformamide and the like. The hydrogen halide or alkyl halide tertiary ammonium salts of the compounds of the invention have appreciable solubility in water.

Among the microorganisms against which the compounds of the invention are active are bacteria, fungi, helminths, coccidii, protozoans and the like. They are particularly active, both in vitro and in vivo, against bacteria. Thus, they can be used for disinfecting and sterilizing, for example of medical and dental equipment, as components of disinfecting solutions. The compounds are particularly useful as antibacterial agents. Some of the compounds are also active in vivo in animals. For applications in which water solubility is of importance, the salts are ordinarily used.

The compounds of the invention (I) are prepared by several methods. Ordinarily the individual reactions are of types generically known to the art, e.g. as methods for the preparation of amines. The reaction condititons are chosen to a large extent for convenience and are generally within the skill of the art to determine, and suitable starting materials are known or can be readily synthesized. Certain of the compounds (I) are prepared by further reaction of others of the compounds (I) or from corresponding novel intermediates (II and III infra), which themselves form aspects of the invention. The methods of preparation include the following:

A. The displacement of the halogen form an alkyl halide by ammonia or, preferably, a primary, secondary or tertiary amine. The starting materials are haloalkyl 3-phenylbenzofurans and haloalkyl 2-nitro-3-phenylbenzofurans. The reactions are carried out at mild to moderate temperatures of 0° to 125° C. in inert solvents such as lower alkyl ketones and aromatic hydrocarbons and monitored by chromatography for disappearance of starting material. When the starting material has reacted, the reaction is quenched.

When the products of this and the other methods described hereinafter are unsubstituted in the 2-position, they are nitrated directly or, alternatively, first halogenated (e.g. brominated) in the 2-position, then nitrated. The direct nitration can be carried out with dinitrogen tetroxide in a solvent such as acetonitrile at moderate temperature (0° to 30° C.). The 2-bromination can be carried out using bromine in a suitable solvent such as dichloromethane and the resulting intermediate compound 2-nitrated using a combination of dinitrogen tetroxide in an inert solvent (such as acetic acid) in the presence of an alkene (e.g. cyclohexene).

The intermediate products of these reactions of the formula

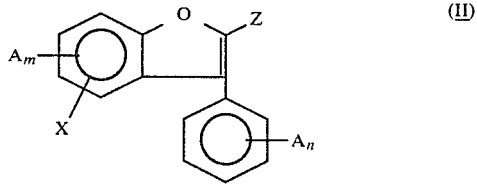

(II)

wherein A is QR— or BD—, R is alkylene of one to three carbon atoms (preferably methylene) or oxyalkylene of two or three carbon atoms, Q is an (N-lower alkanoyl)amino group derived from a primary or secondary amine, B is an unsubstituted tetrazole, D is a carbon-carbon bond or methylene, m and n are zero or one, the sum of m and n is one, Z is hydrogen or bromine and X is hydrogen, methyl or ethyl are novel and constitute a distinct aspect of the invention.

B. The reaction of a haloalkylbenzofuran with hexamethylenetetramine followed by decomposition of the resulting complex. The complex is decomposed by reaction with a strong acid (such as a mineral acid, e.g. hydrochloric acid), as illustrated by Example 17.

C. Blocking and deblocking. When the substituent —R—Q in the final compound is to be amino acid, it is frequently desirable to block the acid until the amino group has been reacted. Deblocking is carried out later if desired. Techniques for this type of conversion are well-known to the amino acid and peptide synthesis art.

D. Preparation of an amine of formula I from the corresponding acid through the amide intermediate. More particularly this involves reacting an alkanoic acid-substituted or carboxylic acid-substituted benzofuran with an acid chloride-producing reagent, e.g. thionyl chloride or phosphorus pentachloride, followed by reaction with ammonia or an amine to provide an amide and finally reduction, e.g. with diborone to provide an amine of formula I.

E. Acylation-reduction of the invention in which —Q is —NH$_2$ or —NHR' can be acylated by reaction with the anhydride of a lower alkanoic acid,

(R"C)$_2$O, to form respectively the compounds in which —Q is

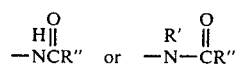

and then reducing (e.g. with diborane) to form the compounds in which —Q is

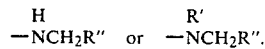

R' and R" are lower alkyl groups herein.

F. Preparation of an amino acid of the invention from an aldehyde-substituted 2-nitro-3-phenylbenzofuran. The aldehyde group is converted to a cyanohydrin, the hydroxy displaced by an amine group and the cyano group hydrolyzed to provide the acid function.

G. Preparation of a tetrazole-substituted-3-phenylbenzofuran of the invention from a cyano-substituted-3-phenylbenzofuran. The cyano-substituted compound is reacted with sodium azide in N,N-dimethylformamide in the presence of ammonium chloride to provide the corresponding tetrazole-substituted-3-phenylbenzofuran. This intermediate (which is unsubstituted in the 2-position of the benzofuran moiety) is converted to the 2-nitro compound of formula I through the 2-bromo intermediate or directly by reaction with dinitrogen tetraoxide (as described previously).

The intermediate compounds

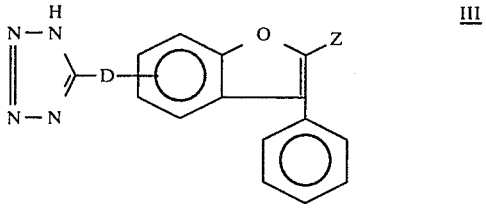

III of this route (wherein Z is hydrogen or bromine and D is a carbon-carbon bond or methylene) are novel and constitute an additional aspect of the invention.

H. Preparation of the compounds of the invention wherein —R— is oxyalkylene. It is preferred to start with hydroxy-substituted-3-phenylbenzofurans, particularly hydroxy-substituted-2-nitro-3-phenylbenzofurans and react them in the presence of a strong base such as sodium hydride with a haloalkylamine. These reactions are generally carried out in an inert solvent such as glyme at the reflux temperature of the reaction mixture.

I. The compounds of the invention are frequently isolated as salts, including hydrated salts. These are readily converted to the free base by neutralizing with a dilute base, such as dilute aqueous sodium hydroxide solution.

J. Preparation of the pharmaceutically acceptable salts of the invention. The salts are readily prepared byh reaction of the corresponding free base (i.e. amine) compound of formula I with the appropriate hydrogen halide or alkyl halide (the latter ordinarily containing not more than about 20 carbon atoms and preferably not more than 12 carbon atoms), optionally in a suitable solvent and evaporating to dryness. Other salts which are not pharmaceutically acceptable may be useful for the synthesis of the basic compounds of the invention or other, acceptable salts or other useful intermediates.

The antimicrobial activity of the compounds is evaluated using a variation of the original agar-plate diffusion method of Vincent and Vincent (e.g. see Vincent, J. G., and Vincent, Helen W., Proc. Soc. Exptl. Biol. Med. 55:162-164, 1944, and Davis, B. D., and Mingioli, E. S., J. Bac. 66:129-136, 1953). Using this test, the compounds of the invention have been found to have a broad spectrum of activity against both gram-positive and gram-negative microorganisms. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are: *Staphylococcus aureus, Bacillus subtilus, Pseudomonas aeruginosa, Escherichia coli, Streptococcus sp.* (strains isolated from dental caries in rats or hamsters at the National Institute of Dental Health and grown in PFY or APT agar) *Asperigillus niger, Candida albicans, Mima polymorpha, Herellea vaginicola, Klebsiella pneumoniae* and *Streptococcus fecaelis.*

These are selected representatives of various bacterial and fungal classes and broad spectrum activity can be predicted as a result of activity against them. All of the compounds of the invention possess antimicrobial activity towards one or more of them. The compounds maintain high activity against the microorganisms either in the absence or presence of ten percent horse serum.

The in vivo antimicrobial activity is determined against infections produced by *Streptococcus pyogenes* C-203 and *Staphylococcus aureus* (Smith) or other bacterial species. The species used is determined by the in vitro antimicrobial spectrum of the compound. Groups of 5 or 10 mice, 18-22 g., are infected intraperitoneally with the test culture. Treatment consists of three oral injections 1, 6 and 24 hours after infection. All mice are observed for extended periods, e.g. for two weeks, and deaths recorded at daily intervals. Control groups consist of one infected, non-treated group and other infected groups receiving varying dosages of the reference standard.

The acute oral toxicity of the compounds of the invention generally is moderate to low compared with the effective oral dose, and they have a good to excellent therapeutic ratio.

The compounds of the invention may be formulated by incorporating them into a conventional pharmaceutical carrier material, either organic or inorganic, which is suitable for oral or parenteral application. For in vitro or topical use, simple aqueous solutions or suspensions are most conveniently employed. For this purpose, concentrations of the order of 100 parts per million up to about 5 parts per thousand are suitable, and the formulation is used by immersing the object to be treated therein, or by local application to an infected area. The amount of compound to be used for, e.g. oral treatment of a microbal infection will be an effective amount less than a toxic amount. The amount to be administered to a subject and route of administration to control an infection will depend on the species of organism, the sex, weight, physical condition of the subject, the locus of the infection, and many other factors, but this judgement is well within the skill of the art. Usually the amount will be less than 100 mg/kg per dose. Conveniently the oral treatment is administered in the form of the usual pharmaceutical preparation such as capsules, tablets, emulsions, solutions, suppositories and the like. Excipients, fillers, coatings, etc., are employed with tablets or capsules, as is well known in the art.

It is often advantageous to combine the compounds of this invention with other antimicrobial compounds such as coccidiostats, anthelmintics, antifungals, antibiotics, steroids or antibacterial agents, or to combine more than one compound described herein in a single formulation.

Certain of the compounds are also active antiparasitics as shown by activity in laboratory tests versus the protozoan *Trichomonas* sp. In view of the outstanding antimicrobial activity of the compounds, they would also be expected to be effective growth promoters in various animal and bird species.

The following examples are given for the purpose of illustrating the invention, but are in no way limiting thereof. The melting points are uncorrected and are in degrees Centigrade.

EXAMPLE 1

A stirred mixture of 5 g. (0.015 mole) of 5-bromomethyl-2-nitro-3-phenylbenzofuran and 7.5 g. (0.075 mole) of N-methylpiperazine in 15 ml. of ethanol is heated at 45° C. for 1 hour. The reaction mixture is evaporated to provide a residue which is extracted with diethyl ether. The ether extracts are washed with water and with a saturated sodium chloride solution and dried. Evaporation of the ether solution provides a yellow oil which is dissolved in diethyl ether and treated while stirring with a solution of 4N hydrochloric acid in isopropanol until the reaction is complete. The solid is stirred in hot ethanol while adding water until it is all in solution. Cooling provides a fluffy yellow product, 1-methyl-4-(2-nitro-3-phenyl-5-benzofuranylmethyl)-piperazine dihydrochloride dihydrate, m.p. 269°-276° C. (dec.), having the structure

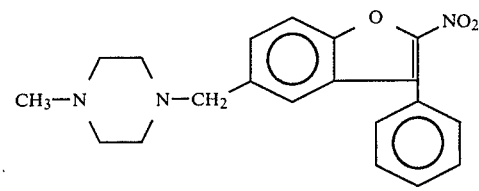

.2HCl.2H$_2$O

| Analysis: | % C | % H | % N |
| --- | --- | --- | --- |
| Calculated for $C_{20}H_{27}O_5N_3Cl_2$: | 52.2; | 5.9; | 9.1 |
| Found: | 52.0; | 5.8; | 9.1. |

EXAMPLE 2

Using the method of Example 1, 5-bromomethyl-2-nitro-3-phenylbenzofuran is reacted with pyrrolidine in ethanol to provide yellow crystals of 2-nitro-3-phenyl-5-(1-pyrrolidylmethyl)benzofuran, m.p. 111°–112.5° C., having the structure

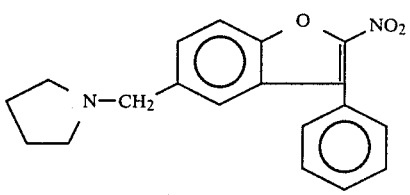

| Analysis: | % C | % H | % N |
| --- | --- | --- | --- |
| Calculated for $C_{19}H_{18}O_3N_2$: | 70.8; | 5.6; | 8.7 |
| Found: | 70.8; | 5.7; | 8.6. |

EXAMPLE 3

Using the method of Example 1, 5-bromomethyl-2-nitro-3-phenylbenzofuran is reacted with 3-(N,N-diethylamino)propylamine in ethanol to provide light tan crystals of 5-[3-(N,N-diethylamino)propylaminomethyl]-2-nitro-3-phenylbenzofuran dihydrochloridemonohydrate, m.p. 143°–150° C., having the structure

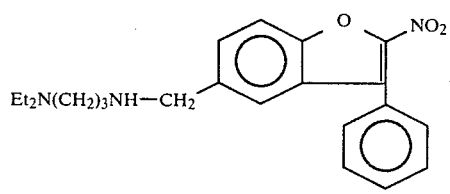

.2HCl.1H$_2$O

| Analysis: | % C | % H | % N |
| --- | --- | --- | --- |
| Calculated for $C_{22}H_{31}O_4N_3Cl_2$: | 55.9; | 6.6; | 9.0 |
| Found: | 55.5; | 7.0; | 9.0. |

EXAMPLE 4

Using the method of Example 1, 5-bromomethyl-2-nitro-3-phenylbenzofuran is reacted with N-hydroxyethylpiperazine in ethanol to provide 4-(2-nitro-3-phenyl-5-benzofuranylmethyl)-1-piperazineethanol dihydrochloride monohydrate, m.p. 248°–266° C. (dec.), having the structure

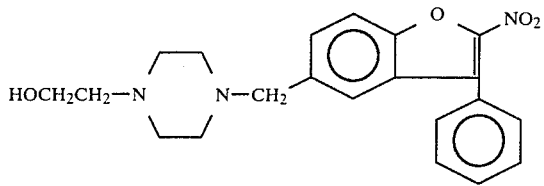

.2HCl.1H$_2$O

| Analysis: | % C | % H | % N |
| --- | --- | --- | --- |
| Calculated for $C_{21}H_{27}O_5N_3Cl_2$: | 53.4; | 5.8; | 8.9 |
| Found: | 53.9; | 5.7; | 9.0. |

EXAMPLE 5

Using the method of Example 1, 5-bromomethyl-2-nitro-3-phenylbenzofuran is reacted with N-phenylpiperazine in ethanol to provide yellow needles of 4-(2-nitro-3-phenyl-5-benzofuranylmethyl)-1-phenylpiperazine, m.p. 155°–157° C., having the structure

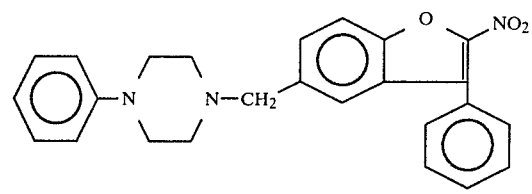

| Analysis: | % C | % H | % N |
| --- | --- | --- | --- |
| Calculated for $C_{25}H_{23}O_3N_3$: | 72.6; | 5.6; | 10.2 |
| Found: | 72.5; | 5.6; | 10.2. |

EXAMPLE 6

Using the method of Example 1, 5-bromomethyl-2-nitro-3-phenylbenzofuran is reacted with morpholine in ethanol to provide yellow crystals of N-(2-nitro-3-phenyl-5-benzofuranylmethyl)-morpholine, m.p. 151°–154° C., having the structure

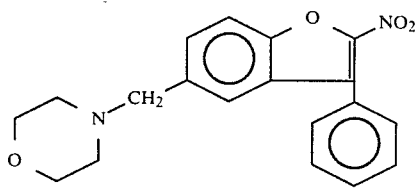

| Analysis: | % C | % H | % N |
| --- | --- | --- | --- |
| Calculated for $C_{19}H_{18}O_4N_2$: | 67.4; | 5.4; | 8.3 |
| Found: | 67.3; | 5.3; | 8.3. |

EXAMPLE 7

Using the method of Example 1, 5-bromomethyl-2-nitro-3-phenylbenzofuran is reacted with N,N'-dimethylaminoethylamine in ethanol to provide yellow solid 5-(N,N'-dimethylaminoethylaminomethyl)-2-nitro-3-phenylbenzofuran dihydrochloride hemihydrate, m.p. 224°-227° C. (dec.), having the structure

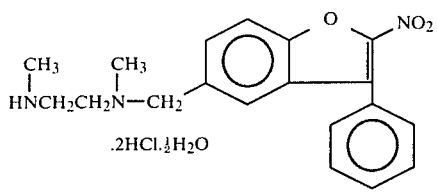

.2HCl.½H₂O

| Analysis: | % C | % H | % N |
|---|---|---|---|
| Calculated for C₁₉H₂₃O₃N₃Cl₂.½H₂O: | 54.2; | 5.7; | 10.0 |
| Found: | 54.0; | 5.3; | 10.2. |

EXAMPLE 8

To a 1.9 g. (0.0056 mole) sample of N-(2-nitro-3-phenyl-5-benzofuranylmethyl)morpholine (the product of Example 6) in 100 ml. of acetone is added 1.0 g. of methyliodide. After setting for one week, an additional 1.0 g. of methyliodide is added. After 1 day of stirring, the precipitated solid is separated by filtration and extracted with 300 ml. of refluxing ethanol to provide yellow crystals of N-methyl-N-(2-nitro-3-phenyl-5-benzofuranylmethyl)morpholinium iodide, m.p. 226°-230° C., having the structure

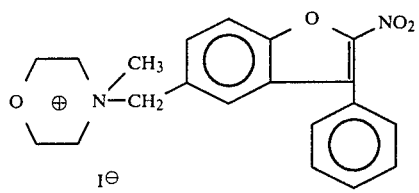

| Analysis: | % C | % H | % N |
|---|---|---|---|
| Calculated for C₂₀H₂₁IN₂O₄: | 50.0; | 4.4; | 5.8 |
| Found: | 50.2; | 4.5; | 6.0. |

EXAMPLE 9

Using the method of Example 8, 4-(2-nitro-3-phenyl-5-benzofuranylmethyl)-1-phenylpiperazine (the product of Example 5) is reacted with methyliodide in acetone to provide 4-methyl-4-(2-nitro-3-phenyl-5-benzofuranylmethyl)-1-phenylpiperazinium iodide, m.p. 120°-125° C., having the structure

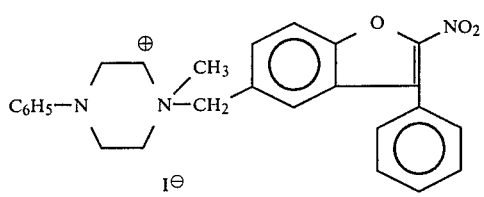

| Analysis: | % C | % H | % N |
|---|---|---|---|
| Calculated for C₂₆H₂₆IN₃O₃: | 56.2; | 4.7; | 7.6 |
| Found: | 56.0; | 4.9; | 7.2. |

EXAMPLE 10

Using the method of Example 8, 2-nitro-3-phenyl-5-(1-pyrrolidylmethyl)benzofuran (the product of Example 2) is reacted with methyliodide in acetone to provide tan solid N-methyl-N-(2-nitro-3-phenyl-5-benzofuranylmethyl)pyrrolidinium iodide, m.p. 235°-237° C., having the structure

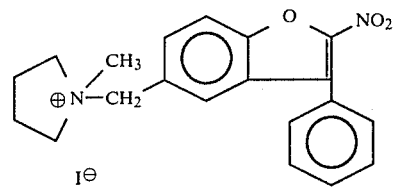

| Analysis: | % C | % H | % N |
|---|---|---|---|
| Calculated for C₂₀H₂₁IN₂O₃: | 51.7; | 4.6; | 6.0 |
| Found: | 51.8; | 4.6; | 6.1. |

EXAMPLE 11

A mixture of 1.7 g. (0.0066 mole) of 1-phenyl-1,3,8-triazaspiro[4.5]decan-4-one (available from the Aldrich Chemical Company) and 2 g. (0.006 mole) of 5-bromomethyl-2-nitro-3-phenylbenzofuran in 50 ml. of acetone is heated at its reflux temperature for about 75 hours. The mixture is cooled to 20° C. and filtered. The precipitate is washed with acetone to provide yellow 1-phenyl-8-N-[(2-nitro-3-phenylbenzofuran-5-yl)methyl]-1,3,8-triazaspiro[4.5]decan-4-one hydrobromide salt, m.p. 243°-244° C., having the structure

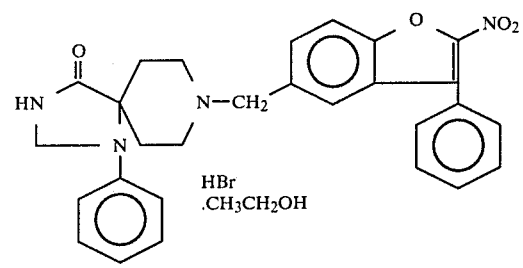

after recrystallization from ethanol.

| Analysis: | % C | % H | % N |
|---|---|---|---|
| Calculated for C₂₈H₂₆N₄O₄.HBr.C₂H₆O: | 59.1; | 5.4; | 9.2 |
| Found: | 58.7; | 5.3; | 9.3. |

EXAMPLE 12

A mixture of 1.04 g. (0.0066 mole) of ethyl isonipecotate and 2 g. (0.006 mole) of 5-bromomethyl-2-nitro-3-phenylbenzofuran in 100 ml. of acetone is heated at reflux for 40 hours. The mixture is cooled and then evaporated to provide a residue which is diluted with diethyl ether. A yellow precipitate is separated by filtration to provide ethyl N-(2-nitro-3-phenylbenzofuran-5-yl)isonipecotate hydrobromide, m.p. 220°–221° C., having the structure

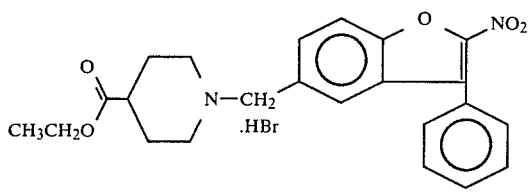

| Analysis: | % C | % H | % N |
|---|---|---|---|
| Calculated for C23H24N2O5.HBr: | 56.4; | 5.1; | 5.7 |
| Found: | 56.3; | 5.4; | 5.6. |

EXAMPLE 13

A mixture of 1.53 g. (0.0099 mole) of ethylisonicotinate (available from the Aldrich Chemical Company) and 3 g. (0.009 mole) of 5-bromomethyl-2-nitro-3-phenylbenzofuran in 100 ml. of acetone is heated at its reflux temperature for about 50 hours. The mixture is cooled and filtered to separate the yellow solid. The solid is washed several times with acetone. The yellow solid is ethyl N-[(2-nitro-3-phenylbenzofuran-5-yl)methyl]isonicotinium bromide, m.p. 238°–239° C., having the structure

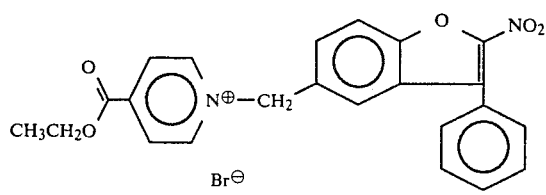

| Analysis: | % C | % H | % N |
|---|---|---|---|
| Calculated for C23H19BrN2O5: | 57.1; | 3.9; | 5.8 |
| Found: | 56.9; | 3.8; | 5.7. |

EXAMPLE 14

A mixture of 0.8 g. of nipecotamide (available from the Aldrich Chemical Company) and 2 g. of 5-bromomethyl-2-nitro-3-phenylbenzofuran in 100 ml. of acetone is heated at its reflux temperature for about 48 hours. The mixture is cooled, and the yellow precipitate is separated by filtration. The filtrate is evaporated to provide a residue. The residue is separated by chromatography in silica gel eluting with dichloromethane. The product is readily separated from starting materials and shown to be N-[(2-nitro-3-phenylbenzofuran-5-yl)methyl]nipecotamide hemihydrate, m.p. 76°–77° C., having the structure

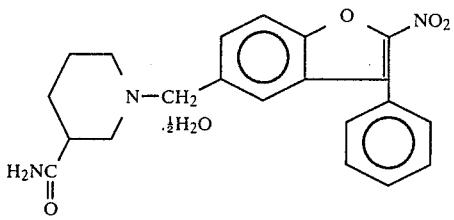

| Analysis: | % C | % H | % N |
|---|---|---|---|
| Calculated for C21H21N3O4.½H2O: | 64.9; | 5.7; | 10.8 |
| Found: | 64.3; | 5.7; | 10.4. |

EXAMPLE 15

A mixture of 2 g. (0.006 mole) of 5-bromomethyl-2-nitro-3-phenylbenzofuran, 0.9 g. (0.006 mole) of L-proline methylesterhydrochloride (available from the Aldrich Chemical Company) and 1.2 g. (0.012 mole) of triethylamine in 100 ml. of toluene is heated at reflux for about 100 hours. The mixture is extracted three times with 50 ml. portions of water. The organic layer is then extracted repeatedly with 50 ml. portions of 3N hydrochloric acid to remove all of the yellow product from the toluene layer. The aqueous layer is neutralized with 10 percent sodium carbonate solution. The aqueous layer is then extracted with dichloromethane until the water is colorless. The dichloromethane layer is dried, then evaporated to provide a residue which is diluted with diethyl ether to provide a brownish precipitate. The solid is removed by filtration, and the filtrate is concentrated to provide a residue. The residue is suspended in 50 ml. of concentrated hydrochloric acid diluted 1:1 with water. The mixture is heated at 90° C. for three hours. The mixture is cooled and filtered to provide a yellow precipitate. The precipitate is washed with water to provide N-[(2-nitro-3-phenylbenzofuran-5-yl)methyl]-L-proline hydrochloride hydrate, m.p. 109°–110° C., having the structure

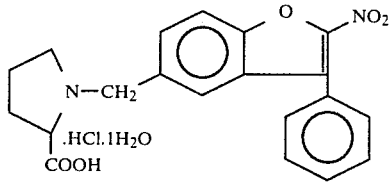

| Analysis: | % C | % H | % N |
|---|---|---|---|
| Calculated for C20H20ClN2O6: | 57.2; | 4.8; | 6.6 |
| Found: | 57.2; | 5.5; | 6.6. |

EXAMPLE 16

A mixture of 0.7 g. (0.006 mole) of pseudothiohydantoin (available from the Aldrich Chemical Company) and 2 g. (0.006 mole) of 5-bromomethyl-2-nitro-3-phenylbenzofuran in 50 ml. of toluene is heated at reflux for about 16 hours. The mixture is cooled, and the light brown solid is removed by filtration. The filtrate is evaporated to provide a residue which is separated into starting material and product by chromatography on silica gel, eluting with benzene. The yellow solid obtained is recrystallized from ethanol to provide yellow solid N-[(2-nitro-3-phenylbenzofuran-5-yl)methyl]-pseudothiohydantoin, m.p. 204°–205° C., having the structure

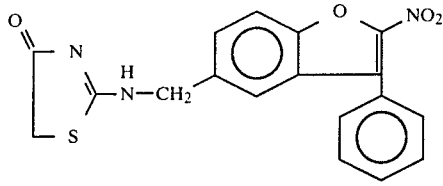

| Analysis: | % C | % H | % N |
|---|---|---|---|
| Calculated for C$_{18}$H$_{13}$N$_3$O$_4$S: | 59.1; | 3.5; | 11.4 |
| Found: | 58.5; | 3.8; | 11.2. |

EXAMPLE 17

To a solution of 3.3 g. (0.010 mole) of 5-bromomethyl-2-nitro-3-phenylbenzofuran in 50 ml. of chloroform is added 1.4 g. (0.010 mole) of hexamethylenetetramine in 25 ml. of chloroform. After stirring for 16 hours a solid precipitate is separated by filtration and rinsed with chloroform. The solid is suspended in a mixture of 100 ml. of 95 percent ethanol and 10 ml. of concentrated hydrochloric acid and stirred. The solution is evaporated to dryness to provide a residue which is recrystallized twice from 3N hydrochloric acid. The product is yellow crystals of 5-aminomethyl-2-nitro-3-phenylbenzofuran hydrochloride hydrate, m.p. 246°–254° C. (dec.), having the structure

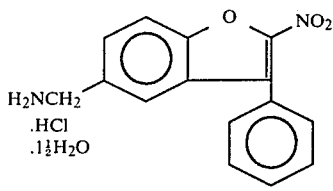

| Analysis: | % C | % H | % N |
|---|---|---|---|
| Calculated for C$_{15}$H$_{12}$N$_2$O$_3$.HCl.1½H$_2$O: | 54.3; | 4.9; | 8.4 |
| Found: | 54.6; | 4.9; | 8.6. |

EXAMPLE 18

A mixture of 1.04 g. (0.006 mole) of L-valine t-butyl ester and 2 g. (0.006 mole) of 5-bromomethyl-2-nitro-3-phenylbenzofuran in 100 ml. of acetone is heated at reflux for about 50 hours. The mixture is cooled, and the solvent is evaporated to provide a residue. The product is separated from the residue by chromatography on silica gel, eluting with benzene. The product is identified by infrared spectral analysis as the tertiary-butyl ester of N-[(2-nitro-3-phenylbenzofuran-5-yl)methyl]-valine. This residue is dissolved in 75 ml. of 6N hydrochloric acid and 25 ml. of ethanol by heating at 75° C. for 4 hours. The reaction mixture is evaporated to provide a residue which is recrystallized from ethanol. The product is light yellow solid N-[(2-nitro-3-phenylbenzofuran-5-yl)methyl]valine hydrochloride, m.p. 183°–184° C., having the structure

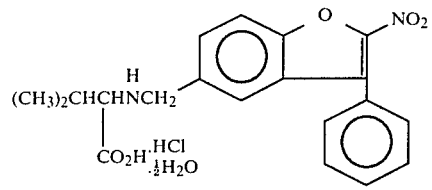

| Analysis: | % C | % H | % N |
|---|---|---|---|
| Calculated for C$_{20}$H$_{20}$N$_2$O$_5$.HCl.¼ H$_2$O: | 58.0; | 5.3; | 6.8 |
| Found: | 58.0; | 5.4; | 6.8. |

EXAMPLE 19

A mixture of 5 ml. of acetic anhydride and 0.3 g. of 5-aminomethyl-2-nitro-3-phenylbenzofuran hydrochloride (from Example 17) is heated on a steam bath for about 30 minutes. The mixture is then partially evaporated to provide a residue which is treated with aqueous isopropanol to form yellow crystals of 5-acetamidomethyl-2-nitro-3-phenylbenzofuran, m.p. 201°–203° C., having the structure

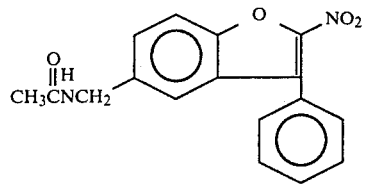

| Analysis: | % C | % H | % N |
|---|---|---|---|
| Calculated for C$_{17}$H$_{14}$N$_2$O$_4$: | 65.8; | 4.5; | 9.0 |
| Found: | 65.6; | 4.5; | 9.0. |

EXAMPLE 20

Step A

A stirred mixture of 2.7 g. (0.010 mole) of 2-nitro-3-phenylbenzofuran-7-aldehyde (described in Belgian Pat. No. 846,502, Example 13) and 20 ml. of diethyl ether is treated with 1.6 g. (0.015 mole) of sodium bisulfite in 10 ml. of water. After 30 minutes, 30 ml. of chloroform is added, followed by 1.5 g. (0.030 mole) of sodium cyanide in 5 ml. of water after an additional 30 minutes. About 0.7 g. of sodium bisulfite is added 1.5 hours later, and the mixture is cooled to 0° C. 30 minutes after the bisulfite addition and maintained for about 16 hours. The organic layer is separated, washed with aqueous sodium bisulfite solution, then with water, and dried over magnesium sulfate. Evaporation of the solution provides a solid which is recrystallized from a chloroform-heptane mixture to provide yellow crystals of α-hydroxy-2-nitro-3-phenylbenzofuran-7-acetonitrile, m.p. 137°–139° C.

| Analysis: | % C | % H | % N |
|---|---|---|---|
| Calculated for $C_{16}H_{10}N_2O_4$: | 65.3; | 3.4; | 9.5 |
| Found: | 64.9; | 3.3; | 9.5. |

Step B

A mixture of 5 g. (0.02 mole) of α-hydroxy-3-phenylbenzofuran-7-acetonitrile and 2 g. of methylamine in 100 ml. of dichloromethane is heated to its reflux temperature, then stirred at 20° C. for 16 hours. The mixture is evaporated to provide a residue which is dissolved in benzene which has been previously saturated with hydrogen chloride. The mixture is heated for 15 minutes on a steam bath, then saturated with petroleum ether, whereupon a white precipitate of α-methylamino-3-phenylbenzofuran-7-acetonitrile hydrochloride forms. A 5 gram sample of this intermediate is suspended in 50 ml. of glacial acetic acid, 5 g. of dinitrogen tetraoxide is added, and the mixture is stirred for 24 hours at 20° C. The volatiles are removed by evaporation to provide a residue which is dissolved in 10 ml. of acetic acid, and the mixture is heated at its reflux temperature while adding 30 ml. of 12N hydrochloric acid. Refluxing is continued for 1 hour, then the mixture is cooled. A green solid is obtained which is recrystallized from glacial acetic acid to provide light green crystals of α-methylamino-2-nitro-3-phenylbenzofuran-7-acetic acid, m.p. 237° C. (dec.), having the structure

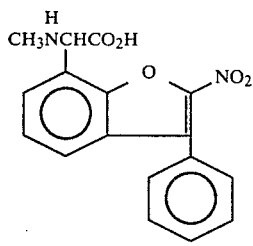

| Analysis: | % C | % H | % N |
|---|---|---|---|
| Calculated for $C_{17}H_{14}N_2O_5 \cdot H_2O$: | 59.3; | 4.6; | 8.1 |
| Found: | 58.7; | 4.3; | 7.9. |

EXAMPLE 21

Step A

A mixture of 61.4 g. (0.28 mole) of 5-cyano-3-phenylbenzofuran (described in U.S. Pat. No. 4,067,993, Example 1), 16.5 g. (0.31 mole) of ammonium chloride and 20.2 g. (0.31 mole) of sodium azide in 250 ml. of N,N-dimethylformamide is stirred at 110°14 120° C. for 16 hours. The mixture is cooled to about 20° C. and poured into about 1 liter of water. A light brown solid forms which is collected by filtration, washed with water, and then recrystallized from ethanol to provide brown crystals of 3-phenyl-5-(1H-tetrazol-5-yl)benzofuran.

Step B

To a solution of 10 g. (0.045 mole) of 3-phenyl-5-(1H-tetrazol-5-yl)benzofuran in 250 ml. of hot dioxane is added 400 ml. of hot dichloromethane. To this solution is added a solution of 7.3 g. (0.045 mole) of bromine in 20 ml. of dichloromethane dropwise over a period of 30 minutes. The resulting solution is stirred for 20 hours. The solid product (2-bromo-3-phenyl-5-(1H-tetrazol-5-yl)benzofuran) is collected by filtration and dried.

Step C

To a solution of 3 g. of the product of Step B in 600 ml. of hot acetic acid is added 1 g. of cyclohexene and 1 g. of dinitrogen tetraoxide. The mixture is heated at its reflux temperature for 16 hours. An additional 1 g. of cyclohexene and 1 g. of dinitrogen tetraoxide is added to the mixture, and heating is continued for 5 hours. The solution is poured into 2 liters of water and stirred. The resulting yellow precipitate is isolated by filtration, washed with water and dried, then recrystallized from aqueous isopropanol to provide yellow crystals of 2-nitro-3-phenyl-5-(1H-tetrazol-5-yl)benzofuran, m.p. 215°-217° C., having the structure

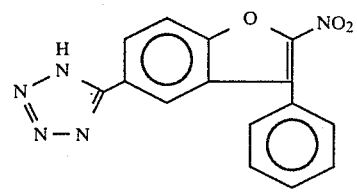

| Analysis: | % C | % H | % N |
|---|---|---|---|
| Calculated for $C_{15}H_9N_5O_3$: | 58.6; | 2.9; | 22.8 |
| Found: | 57.9; | 3.2; | 21.8. |

The structure of the product is confirmed by infrared and mass spectral analysis. The presence of some isopropanol and some water is determined.

EXAMPLE 22

To a solution of 2 g. (0.008 mole) of 6-hydroxy-2-nitro-3-phenylbenzofuran (described in U.S. Pat. No. 3,927,037, Example 2) in 25 ml. of glyme is added a solution of 0.016 mole of sodium hydride in 20 ml. of glyme. To this solution is added 1.2 g. (0.008 mole) of N,N-dimethyl-N-(2-chloroethyl)amine hydrochloride. The mixture is heated to its reflux temperature and maintained at reflux for 6 hours. The reaction mixture is extracted thrice with diethyl ether, the ether is washed with water and saturated sodium chloride solution and then dried. The ether extracts are treated while stirring with hydrogen chloride gas. A yellow residue is separated and washed with diethyl ether, then recrystallized from isopropanol to provide N,N-dimethyl-2-(2-nitro-3-phenyl-6-benzofuranyloxy)ethylamine hydrochloride, m.p. 231°-235° C. (dec.), having the structure

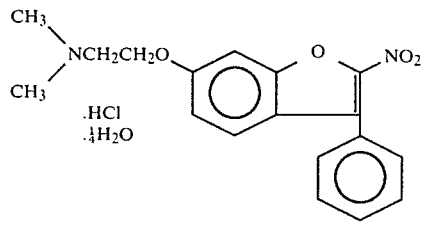

| Analysis: | % C | % H | % N |
|---|---|---|---|
| Calculated for $C_{18}H_{19}ClN_2O_4 \cdot \frac{1}{4}H_2O$: | 58.9; | 5.4; | 7.6 |

-continued

| Analysis: | % C | % H | % N |
|---|---|---|---|
| Found: | 58.7; | 5.4; | 7.6. |

EXAMPLE 23

To a suspension of 1.2 g. of sodium hydride in 25 ml. of glyme is added a solution of 2 g. (0.008 mole) of 6-hydroxy-2-nitro-3-phenylbenzofuran in 25 ml. of glyme, 1.9 g. (0.012 mole) of 3-(N,N-dimethylamino)-propylchloride hydrochloride is added and the mixture is heated to its reflux temperature and maintained at reflux for 2 hours. The mixture is then evaporated, and the residue is diluted with water. The aqueous residue is extracted 4 times with diethyl ether. The ether extracts are washed with water and saturated sodium chloride solution and dried. The ether solution is treated with hydrogen chloride gas, and a solid precipitate which forms is separated by decantation and recrystallized from water. The yellow product solid is N,N-dimethyl-3-(2-nitro-3-phenyl-6-benzofuranyloxy)propylamine hydrochloride hydrate, m.p. 221°–224° C., having the structure

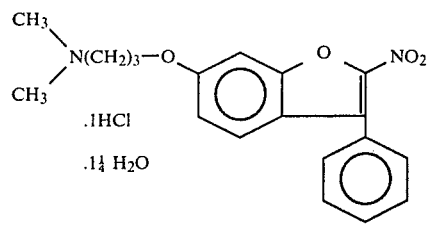

| Analysis: | % C | % H | % N |
|---|---|---|---|
| Calculated for $C_{19}H_{21}ClN_2O_4 \cdot 1\frac{1}{4} H_2O$: | 57.1; | 5.9; | 7.0 |
| Found: | 56.9; | 5.9; | 6.9. |

EXAMPLE 24

Step A

A mixture of 40 g. of 4-methylphenol, 100 g. of 4-bromo-α-bromoacetophenone (both available from the Aldrich Chemical Company), 80 g. of potassium carbonate and 1 liter of acetone is heated to its reflux temperature and maintained at reflux with stirring for 64 hours. To this mixture is added 10 g. more of potassium carbonate, and refluxing is continued for an additional 5 hours. The mixture is cooled, filtered and evaporated to provide a residue of α-(4-methylphenoxy)-4-bromoacetophenone as light brown crystals after recrystallization from aqueous isopropanol.

Step B

The product of Step A is mixed with 500 g. of polyphosphoric acid and heated at 100° C. for 2 hours with stirring, then decanted into 1 liter of ice water. The aqueous mixture is extracted with diethyl ether, and the ether extracts are washed with saturated sodium chloride solution and dried. The solution is evaporated to provide a brown oil which is distilled at 160°–170° C. at 0.25 mm. of Hg to provide 3-(4-bromophenyl)-5-methylbenzofuran.

Step C

The product of Step B is reacted in a Grignard reaction with 5 g. of magnesium turnings in 25 ml. of tetrahydrofuran (by adding the product of Step B in 150 ml. of tetrahydrofuran at a rate sufficient to sustain refluxing). Refluxing is continued for an additional 3 hours, after which the mixture is stirred overnight at about 20° C. To this reaction mixture is added gaseous carbon dioxide over a period of 1 hour, the mixture being maintained at reflux during the second half of the hour. The reaction mixture is cooled and cautiously added to 50 ml. of 6N hydrochloric acid, then evaporated to provide a residue which is recrystallized from acetic acid to provide tan crystals of 4-(5-methyl-3-benzofuranyl)benzoic acid.

Step D

A mixture of 22.5 g. of the product of Step C, 2 g. of cupric nitrate and 100 ml. of acetonitrile is cooled with an ice bath, and 10 g. of dinitrogen tetraoxide in 20 ml. of acetonitrile is added over a period of 10 minutes. The ice bath is removed and the mixture is stirred at 20° C. for 4 hours, evaporated, partially cooled and filtered. The residue is recrystallized from aqueous N,N-dimethylformamide. The product is yellow crystals of 4-(5-methyl-2-nitro-3-benzofuranyl)benzoic acid, m.p. 258° C. (dec.).

| Analysis: | % C | % H | % N |
|---|---|---|---|
| Calculated for $C_{16}H_{11}NO_5$: | 64.6; | 3.7; | 4.7 |
| Found: | 64.2; | 3.7; | 4.8. |

Step E

To a solution of the product of Step D in 200 ml. of tetrahydrofuran is added 150 ml. of 1N diborane. The mixture is heated and maintained at reflux for 2 hours, 100 ml. of 3N sulfuric acid is added and refluxing is continued for an additional hour. The mixture is then evaporated to provide a residue which is recrystallized from aqueous isopropanol to form yellow crystals of 3-(4-hydroxymethyl)phenyl-5-methyl-2-nitrobenzofuran, m.p. 145°–147° C.

| Analysis: | % C | % H | % N |
|---|---|---|---|
| Calculated for $C_{16}H_{13}NO_4$: | 67.8; | 4.6; | 4.6 |
| Found: | 67.4; | 4.6; | 4.7. |

Step F

To a 6 g. sample of the product of Step E is added slowly 20 ml. of thionyl chloride. The mixture is then heated on a steam bath for 15 minutes and evaporated to provide a residue which is treated with benzene and re-evaporated twice. The resulting residue crystallizes when suspended in ethanol. The product is 3-(4-chloromethyl)phenyl-5-methyl-2-nitrobenzofuran, m.p. 116°–120° C.

| Analysis: | % C | % H | % N |
|---|---|---|---|
| Calculated for $C_{16}H_{12}ClNO_3$: | 63.7; | 4.0; | 4.6 |
| Found: | 63.8; | 4.0; | 4.6. |

Step G

A suspension of 1 g. of the product of Step F in 15 ml. of ethanol and 5 g. of diethylamine is heated on a steam bath for 2 hours. The mixture is evaporated to provide a residue which is recrystallized from aqueous isopropanol to form yellow crystals of 3-(4-diethylaminomethyl)phenyl-5-methyl-2-nitrobenzofuran, m.p. 117°–119° C., having the structure

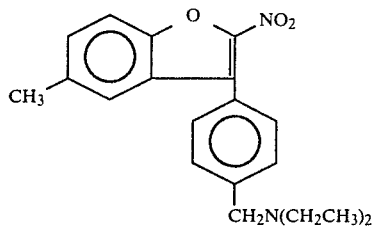

| Analysis: | % C | % H | % N |
| --- | --- | --- | --- |
| Calculated for $C_{20}H_{22}N_2O_3$: | 71.0; | 6.6; | 8.3 |
| Found: | 70.9; | 6.5; | 8.0. |

EXAMPLE 25

To a solution of 1 g. of 3-(4-chloromethyl)phenyl-5-methyl-2-nitrobenzofuran (described in Step F of the previous example) in 25 ml. of ethanol is added 25 ml. of ethanol which is saturated with methylamine gas. Methylamine is bubbled into the reaction mixture over 20 minutes while heating on a steam bath, and heating is continued for 2 hours. The reaction mixture is evaporated, the residue is dissolved in chloroform and the solution is washed with dilute sodium hydroxide solution and dried. The dried solution is evaporated to provide a residue which is dissolved in isopropanol and treated with hydrogen chloride gas until the solution is acidic. Yellow crystals of 5-methyl-3-(4-methylaminomethyl)phenyl-2-nitrobenzofuran hydrochloride, m.p. 250° C. (dec.), are formed. The structure of this product is as follows

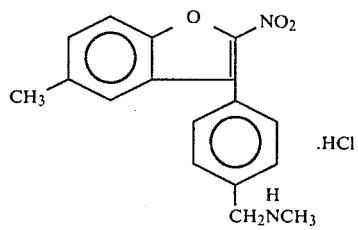

| Analysis: | % C | % H | % N |
| --- | --- | --- | --- |
| Calculated for $C_{17}H_{16}N_2O_3.HCl$: | 61.4; | 5.1; | 8.4 |
| Found: | 61.9; | 5.3; | 8.2. |

EXAMPLE 26

Step A

To a 2.4 g. sample of 4-(5-methyl-2-nitro-3-benzofuranyl)benzoic acid (described in Step D of Example 24) is added 15 ml. of thionyl chloride and 3 drops of N,N-dimethylformamide. The mixture is heated on a steam bath for 30 minutes, then evaporated to provide a residue. The residue is dissolved in 50 ml. of chloroform, ammonia gas is bubbled into the solution for 15 minutes, an additional 200 ml. of chloroform is added, and the solution is washed twice with water and dried. The solution is then evaporated to provide a yellow residue which is recrystallized from aqueous N,N-dimethylformamide. The product is yellow crystals of 4-(5-methyl-2-nitro-3-benzofuranyl)benzamide, m.p. 227°–229° C.

| Analysis: | % C | % H | % N |
| --- | --- | --- | --- |
| Calculated for $C_{16}H_{12}N_2O_4$: | 64.9; | 4.1; | 9.4 |
| Found: | 64.6; | 4.0; | 9.6. |

Step B

To a suspension of 1.3 g. of the product of Step A in 30 ml. of tetrahydrofuran is added 20 ml. of 1N diborane in tetrahydrofuran. The solution is stirred at 20° C. for 20 hours, then 20 ml. of 6N hydrochloric acid is added. The mixture is heated at reflux for ½ hour, then evaporated to provide a residue which is treated with 10 percent sodium hydroxide solution until basic. The resulting aqueous solution is extracted with chloroform, and the extracts are dried, then evaporated to provide a residue which is recrystallized from a chloroform-heptane mixture to provide a first crop of 0.2 g. of yellow solid which is found to be starting material. A second crop of 0.7 g. of yellow crystal is obtained which is dissolved in isopropanol and treated with gaseous hydrogen chloride to provide yellow crystals of 3-(4-aminomethyl)phenyl-5-methyl-2-nitrobenzofuran hydrochloride, m.p. 271° C. (dec.), having the formula

| Analysis: | % C | % H | % N |
| --- | --- | --- | --- |
| Calculated for $C_{16}H_{14}N_2O_3.HCl$: | 60.3; | 4.7; | 8.8 |
| Found: | 60.1; | 4.8; | 8.8. |

EXAMPLE 27

Using the method of Example 1, and starting with 7-bromomethyl-2-nitro-3-phenylbenzofuran and N-methylaminoethylamine the product obtained is 7-(N-methylaminoethylaminomethyl)-2-nitro-3-phenylbenzofuran dihydrochloride having the structure

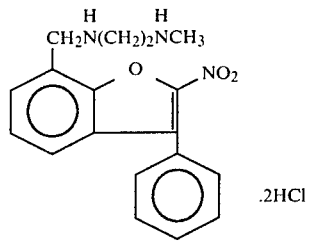

EXAMPLE 28

Starting with 3-(4'-bromomethyl phenyl)-2-bromobenzofuran, nitration with dinitrogen tetraoxide in acetic acid in the presence of cyclohexene-4-carboxylic acid provides 3-(4'bromomethyl phenyl)-2-nitrobenzofuran which is reacted according to the method of Example 1 with N,N'-dimethylaminoethylamine. The product obtained is 3-[4'-(N,N'-dimethylaminoethylaminomethyl)phenyl]-2-nitrobenzofuran having the structure

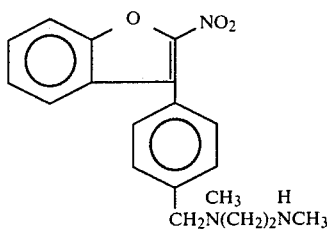

EXAMPLE 29

Using the method of Example 23 and starting with 7-hydroxy-2-nitro-3-phenylbenzofuran and N-methylamino ethylchloride, the product obtained is N-methyl-3-(2-nitro-3-phenyl-7-benzofuranyloxy)ethylamine hydrochloride having the structure

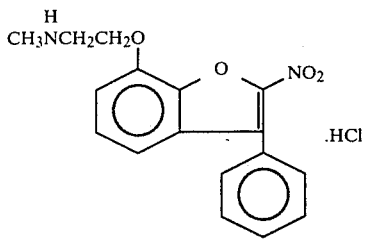

EXAMPLE 30

Using the method of Example 6, 5-bromomethyl-2-nitro-3-phenylbenzofuran is reacted with piperidine in ethanol to provide N-(2-nitro-3-phenylbenzofuranylmethyl)piperidine having the structure

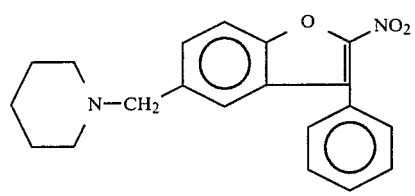

EXAMPLE 31

Step A

A mixture of 4.6 g. (0.02 mole) of 5-cyanomethyl-3-phenylbenzofuran, 1.5 g. of sodium azide and 1.2 g. of ammonium chloride in 15 ml. of N,N-dimethylformaide is heated at 110° C. for 20 hours. The reaction mixture is poured into 200 ml. of water and stirred. The mixture is extracted with 50 ml. of chloroform. The extracts are washed with water, then dried over magnesium sulfate. Evaporation provides a residue which is recrystallized from ethyl acetate to provide 3-phenyl-5-(1H-tetrazol-5yl)methylbenzofuran.

Step B

To a stirred solution of 2.8 g. (0.01 mole) of 5-tetrazolylmethyl-3-phenylbenzofuran in 100 ml. of chloroform and 20 ml. of dioxane is added dropwise 1.6 g. (0.01 mole) of bromine. After 45 minutes the mixture is cooled to 0° C., then the product is separated by filtration and washed with chloroform. Recrystallization from aqueous ethanol provides 2-bromo-3-phenyl-5-(1H-tetrazol-5yl)methylbenzofuran m.p. 215°–217° C.

Step C

To a stirred solution of 1.9 g. (0.005 mole) of 2-bromo-3-phenyl-5-tetrazolylmethylbenzofuran in 50 ml. of warm acetic acid and 1 ml. of cyclohexene is added 1 g. of dinitrogen tetraoxide. The mixture is heated on a steam bath for 30 minutes, then cooled to ice bath temperature. The product is separated by filtration, washed with acetic acid and diethyl ether and recrystallized from ethanol to provide yellow needles of 2-nitro-3-phenyl-5(1H-tetrazol-5-ylmethyl)benzofuran, m.p. 245°–247° C. having the structure

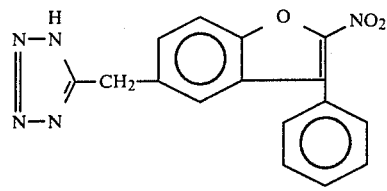

| Analysis: | % C | % H | % N |
|---|---|---|---|
| Calculated for $C_{16}H_{11}N_5O_3$: | 59.8; | 3.1; | 21.8 |
| Found: | 59.6; | 3.5; | 21.7. |

EXAMPLE 32

The compounds are tested against the following bacteria:
Streptococcus species
*Escherichia coli*

The standard plate dilution method for microbial susceptibility to antibiotics is used, employing as a culture medium tryptone soy agar (oxoid) of the following composition:

| | |
|---|---|
| Oxoid tryptone | 15 g. |
| Oxoid soy peptone | 5 g. |
| Sodium chloride | 5 g. |
| Oxoid agar-agar No. 3 | 15 g. |

| -continued | |
|---|---|
| Water | 1 liter |

The tests may optionally be conducted in the absence or in the presence of 10 percent horse serum.

In the tests, the selected compound is added to the agar medium to give concentrations of zero, 0.1, 1, 10 and 100 milligrams per liter. Series of plates with these concentrations are prepared for each compound. Aliquots of broth cultures of each of the species of microorganisms (bacteria) are inoculated onto the agar plates containing the various compound concentrations. The plates are incubated at 37° C. in a 10 percent carbon dioxide atmosphere for 18 to 24 hours. A microbial growth on each plate is then read visually, and minimal inhibitory concentrations are recorded.

The following table shows the results obtained in tests of the compounds of Examples 1–26 (p indicating partial inhibition at the level specified and X indicating inactivity at the highest level tested (100 milligrams per liter)). The following results are obtained in the absence of horse serum.

| | Microorganism | |
|---|---|---|
| Compound(1) | Strep. | E.Coli |
| 1 | 1 | 1p |
| 2 | 10 | 10 |
| 3 | 1 | 1p |
| 4 | 1 | 1p |
| 5 | 10 | X |
| 6 | 10 | 10 |
| 7 | 1 | 1p |
| 8 | 10 | 100p |
| 9 | 1 | 100 |
| 10 | 1 | 10p |
| 11 | 10 | X |
| 12 | 10p | 10p |
| 13 | 10 | 100 |
| 14 | 10 | 1p |
| 15 | 1 | 10p |
| 16 | 10 | 1p |
| 17 | 0.1 | 1 |
| 18 | 1 | 10 |
| 19 | 10 | 1 |
| 20 | 1p | 100 |
| 21 | 1 | 1 |
| 22 | 1 | 1p |
| 23 | 1 | 10p |
| 24 | 10 | 10 |
| 25 | 10p | 1p |
| 26 | 10 | 1 |

(1)The compounds are designated by the example numbers showing their preparation herein.

What is claimed is:

1. A compound of the formula

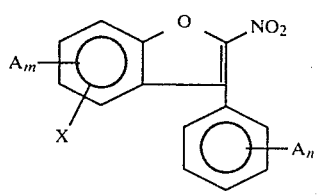

wherein
A is BD—,
B is an unsubstituted tetrazole ring,
D is a carbon-carbon bond or methylene,
m and n are zero or one, the sum of m and n is one and
X is hydrogen, methyl or ethyl.

2. A compound according to claim 1 wherein m is one.

3. A compound according to claim 1 wherein n is one.

4. A compound of the formula

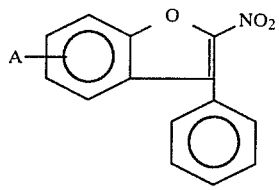

wherein
A is BD—,
B is an unsubstituted tetrazole ring and
D is a carbon-carbon bond or methylene.

5. A compound of the formula

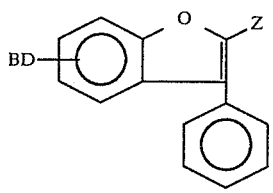

wherein
B is an unsubstituted tetrazole ring,
D is a carbon-carbon bond or methylene and
Z is hydrogen or bromine.

6. 3-Phenyl-5-(1H-tetrazol-5-yl)benzofuran according to claim 5.

7. 2-Bromo-3-phenyl-5-(1H-tetrazol-5-yl)benzofuran according to claim 5.

8. 3-Phenyl-5-(1H-tetrazol-5yl)methylbenzofuran according to claim 5.

9. 2-Bromo-3-phenyl-5-(1H-tetrazol-5yl)methylbenzofuran according to claim 5.

10. 2-Nitro-3-phenyl-5(1H-tetrazol-5-yl)benzofuran according to claim 1.

11. 2-Nitro-3-phenyl-5(1H-tetrazol-5-ylmethyl)benzofuran according to claim 1.

12. A method for arresting or inhibiting the growth of microorganisms comprising contacting said microorganisms with a compound according to claim 1 in an amount sufficient to inhibit the growth of said microorganisms.

13. A method for arresting or inhibiting the growth of bacteria comprising contacting said bacteria with a compound according to claim 1 in an amount sufficient to inhibit the growth of said bacteria.

14. An antimicrobial composition comprising an antimicrobially effective amount of a compound according to claim 1 dispersed in a pharmaceutically acceptable extending medium.

15. An antibacterial composition comprising an antibacterially effective amount of a compound according to claim 1 dispersed in a pharmaceutically acceptable extending medium.

* * * * *